US008924232B2

(12) United States Patent
Alsafadi et al.

(10) Patent No.: US 8,924,232 B2
(45) Date of Patent: Dec. 30, 2014

(54) DEVICE AND METHOD FOR COMPARING MOLECULAR SIGNATURES

(75) Inventors: Yasser H. Alsafadi, Yorktown Heights, NY (US); Nilanjana Banerjee, Armonk, NY (US); Vinay Varadan, New York, NY (US); Angel J. Janevski, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 155 days.

(21) Appl. No.: 13/319,567

(22) PCT Filed: May 5, 2010

(86) PCT No.: PCT/IB2010/051969
§ 371 (c)(1),
(2), (4) Date: Jan. 20, 2012

(87) PCT Pub. No.: WO2010/131162
PCT Pub. Date: Nov. 18, 2010

(65) Prior Publication Data
US 2012/0109678 A1    May 3, 2012

Related U.S. Application Data

(60) Provisional application No. 61/176,989, filed on May 11, 2009.

(51) Int. Cl.
*G06Q 50/24* (2012.01)
*G06F 19/18* (2011.01)
*G06Q 50/22* (2012.01)

(52) U.S. Cl.
CPC ............... *G06F 19/18* (2013.01); *G06Q 50/22* (2013.01)

USPC ................. 705/2; 435/6.14; 435/6.16; 705/3

(58) Field of Classification Search
CPC .......... C12Q 2600/158; C12Q 1/6886; C12Q 2600/118
USPC .................................. 435/6; 702/19; 705/2, 3
See application file for complete search history.

(56) References Cited

U.S. PATENT DOCUMENTS

| | | | | |
|---|---|---|---|---|
| 6,263,287 B1* | 7/2001 | Zheng et al. | ..................... | 702/20 |
| 6,453,241 B1* | 9/2002 | Bassett et al. | ..................... | 702/19 |
| 6,647,341 B1* | 11/2003 | Golub et al. | ..................... | 702/19 |
| 7,592,138 B2* | 9/2009 | Hare et al. | ................... | 435/6.16 |
| 7,711,492 B2* | 5/2010 | Staudt et al. | ..................... | 702/19 |
| 7,960,359 B2* | 6/2011 | Brown et al. | ............... | 514/44 R |
| 8,058,250 B2* | 11/2011 | Brown et al. | ................. | 514/44 A |
| 8,131,475 B2* | 3/2012 | Staudt et al. | ..................... | 702/19 |
| 8,252,760 B2* | 8/2012 | Hernando et al. | ........... | 514/44 A |
| 8,321,137 B2* | 11/2012 | Tran et al. | ....................... | 702/19 |
| 2002/0115070 A1* | 8/2002 | Tamayo et al. | ................... | 435/6 |
| 2004/0053317 A1* | 3/2004 | Glinskii | ............................ | 435/6 |
| 2005/0069863 A1* | 3/2005 | Moraleda et al. | ................. | 435/4 |
| 2005/0071087 A1* | 3/2005 | Anderson | ........................ | 702/19 |
| 2005/0112630 A1* | 5/2005 | Shaughnessy et al. | ........... | 435/6 |

(Continued)

*Primary Examiner* — Hiep V Nguyen
*Assistant Examiner* — Teresa Woods

(57) ABSTRACT

A method (10) for clinical decision support by comparison of multiple molecular signatures of biological data is provided. The method comprises comparing at least two of said molecular signatures are different kinds of molecular signatures. Furthermore, a device (70), a system (100), and a computer program product (200) and a use for clinical decision support, performing the steps according to the method (10) is provided.

9 Claims, 7 Drawing Sheets

(56) References Cited

U.S. PATENT DOCUMENTS

| | | |
|---|---|---|
| 2005/0142573 A1* | 6/2005 | Glinskii .............................. 435/6 |
| 2005/0158756 A1* | 7/2005 | Hare et al. ......................... 435/6 |
| 2006/0211025 A1* | 9/2006 | Su et al. ............................ 435/6 |
| 2008/0020379 A1* | 1/2008 | Agan et al. ........................ 435/6 |
| 2008/0292546 A1* | 11/2008 | Clarke et al. ................. 424/1.49 |
| 2009/0305295 A1* | 12/2009 | Hare et al. ......................... 435/6 |
| 2010/0009348 A1* | 1/2010 | Romanov et al. ................. 435/6 |

* cited by examiner

DEVICE AND METHOD FOR COMPARING MOLECULAR SIGNATURES

FIELD OF THE INVENTION

This invention pertains in general to the field of bioinformatics. More particularly the invention relates to a method for clinical decision support by comparing multiple molecular signatures. The invention also relates to a device for comparing multiple molecular signatures, a system for clinical decision support, a computer-readable medium and a use for analyzing clinical data.

BACKGROUND OF THE INVENTION

It is known that high-throughput molecular profiling of biological samples has resulted in molecular signatures used to stratify the samples into particular categories.

This ranges from answering questions in the context of screening and diagnosis, to disease sub-typing and predicting response to treatment/therapy regiments. Many signatures are known within the art, in various stages of biological and clinical validation. Tests for predicting aggressiveness of breast cancer have for example been provided in commercial applications such as MammaPrint from Agendia or Oncotype DX from Genomic Health.

The fast development within the art has given rise to many molecular signatures that stratify patients into particular categories this data, is often incoherent and diverse, since no particular standard exists. The complex nature of biological systems, and the way these are studied, also makes it difficult to compare sets of genomic identities of different origin.

For example, if you have microarray-based assay that screens gene expression patterns significant for blood diseases, parts of these patterns may be the same as gene expression signatures significant for increased risk of stroke. However, even though parts of the signatures are similar, there is not disclosed within the art how to assess thematic overlap.

Hence, an improved method for analysis of biological data would be advantageous and in particular a method allowing for improved clinical decision support, increased flexibility, cost-effectiveness, speed and/or analytical precision would be advantageous.

SUMMARY OF THE INVENTION

Accordingly, the present invention seeks to mitigate, alleviate or eliminate one or more of the above-identified deficiencies in the art and disadvantages singly or in any combination. This object is achieved by providing a method, a device, a system, a computer-readable medium and a use for clinical decision support, according to the appended independent patent claims.

A general idea of the present invention is to correlate genetic information with molecular signatures and rank the molecular signatures.

According to a first aspect of the invention, a method is provided, comprising the step of obtaining genetic information. Furthermore, the method comprises a step of obtaining primary biological data corresponding to the genetic information from a knowledge database. The genetic information is then ordered according to the primary biological data. The method also comprises the step of obtaining multiple molecular signatures from a signature data repository. The method further comprises obtaining secondary biological data corresponding to each molecular signature from the knowledge database. The method comprises a step of sorting said molecular signatures according to the correspondence of said secondary biological data and said primary biological data, to form a ranking of said molecular signatures. Finally, the method comprises a step of generating an output signal indicative of a clinical decision based on said ordered genetic information and said ranking of the molecular signatures.

According to a second aspect of the invention, a device for clinical decision support is provided, comprising units configured to perform the steps according to the first aspect of the invention, when said units are operatively connected to each other.

According to a third aspect of the invention, a system for clinical decision support is provided. The system comprises a device according to the second aspect of the invention. Furthermore, the system comprises a knowledge database and a signature data repository. The system also comprises a workstation. The device, knowledge database, signature data repository and workstation are operatively connected by a connecting network.

According to a fourth aspect of the invention, a computer-readable medium having embodied thereon a computer program for processing by a computer is provided. The computer program comprises a code segment for performing the method according to the first aspect of the invention.

According to a fifth aspect of the invention, use of the method according to the first aspect, the device according to the second aspect or the system according to the third aspect, for statistical analysis of clinical data is provided.

Embodiments of the invention are defined in the dependent claims.

The method, device, system, and computer-readable medium respectively has at least the advantage that it allows clinical decision support based on comparing multiple molecular signatures, wherein at least two of said molecular signatures are different kinds of molecular signatures. This provides enhanced possibilities for drawing conclusions from genetic information.

BRIEF DESCRIPTION OF THE DRAWINGS

These and other aspects, features and advantages of which the invention is capable of will be apparent and elucidated from the following description of embodiments of the present invention, reference being made to the accompanying drawings, according to which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Generally, a gene set G of genes is represented by an ID set of N identifiers. The ID set is first aligned against itself in a matrix. The overlap between the identifier sets IDi and IDj of sets Gi and Gj is defined as the absolute similarity according to the formula:

$$AS(i,j)=AS(j,i)=|ID_i ID_j|$$

i.e. the cardinality of the intersection between their corresponding ID sets. Relative similarity RS(i,j) between the two identifier sets i, j is defined as:

$$RS(i,j)=AS(i,j)/|ID_i|$$

and relative similarly RS(j,i) between the two identifier sets j, i is defined as:

$$RS(j,i)=AS(j,i)/|ID_j|$$

To measure similarity for a set of identifiers against a collection of C sets, a Collective Similarity CSi is built for identifier set IDi, according to the formula:

$$CSi=<RS(i,j)>$$

where j=1, . . . , C.

Figure 1:
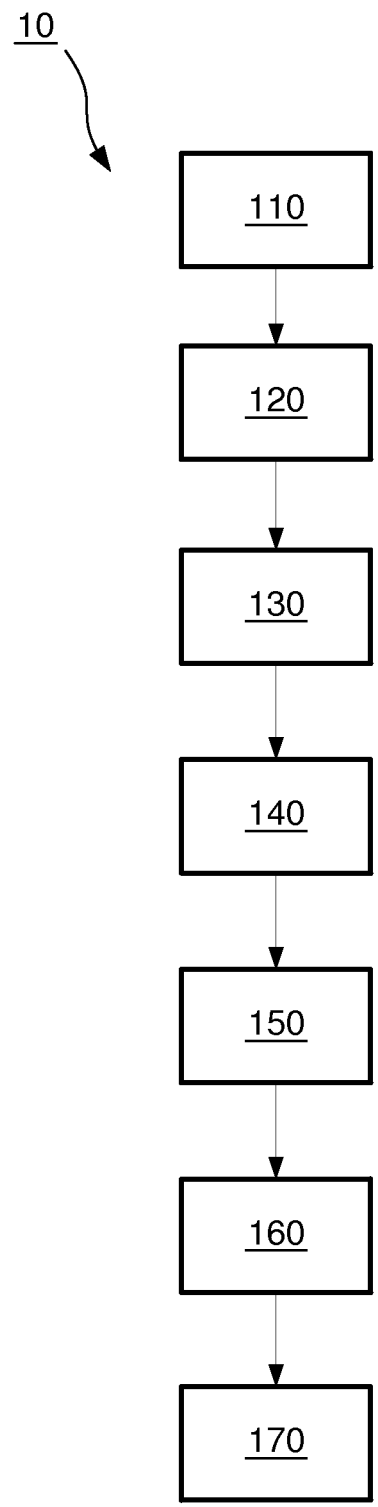
FIG. 1 is a flowchart of a method according to an embodiment.

In an embodiment according to FIG. 1, a method 10 is provided for using gene sets to reflect various biological processes implicated in cancer. This is done through thematic clusters used to describe and compare four breast cancer prognostic signatures. Genetic information in the form of 25 gene sets is obtained in a step 110 from the database MsigDB (http://www.broad.mit.edu/gsea/msigdb/), well known to a person skilled in the art. In an embodiment, curated gene sets are used specifically because they are derived by focusing on a relatively narrow set of biological processes compared to a prognostic signature. One group of gene sets are chosen for their relation to a breast cancer-related signature and another group of gene sets are chosen for control purposes, since they are unlikely to capture breast cancer-related processes. The 25 curated gene sets are shown in table 1.

TABLE 1

25 curated gene sets from MSigDB.

| MSigDB Name | Short name |
|---|---|
| BREAST CANCER-RELATED GROUP | |
| AMIPATHWAY | amip |
| APOPTOSIS | apop |
| BASSO_HCL_DIFF | hcld |
| BLOOD_CLOTTING_CASCADE | clot |
| BREAST_CANCER_ESTROGEN_SIGNALING | bces |
| BRENTANI_ANGIOGENESIS | agen |
| HSA05215_PROSTATE_CANCER | pros |
| HYPOXIA_REVIEW | hypo |
| IL10PATHWAY | il10 |
| IL17PATHWAY | il17 |
| IL22BPPATHWAY | il22 |
| INFLAMMATORY_RESPONSE_PATHWAY | infp |

TABLE 1-continued 25 curated gene sets from MSigDB.

| MSigDB Name | Short name |
|---|---|
| MAPKPATHWAY | mapk |
| P53PATHWAY | p53 |
| SRC_ONCOGENIC_SIGNATURE | srco |
| TRYPTOPHAN_METABOLISM | t_met |
| TUMOR_SUPRESSOR | tsup |
| VEGFPATHWAY | vegf |
| WNT_SIGNALING | wnts |
| WNTPATHWAY | wntp |
| CONTROL GROUP | |
| CARBON_FIXATION | c_fix |
| KREBS_TCA_CYCLE | k_tca |
| METHIONINE_METABOLISM | m_met |
| PLCPATHWAY | plcp |
| UBIQUITIN_MEDIATED_PROTEOLYSIS | ubiq |

Next, primary biological data corresponding to each gene set is obtained in a step 120 from the Gene Ontology (GO) database (http://www.geneontology.org/), well known to a person skilled in the art.

Figure 2:
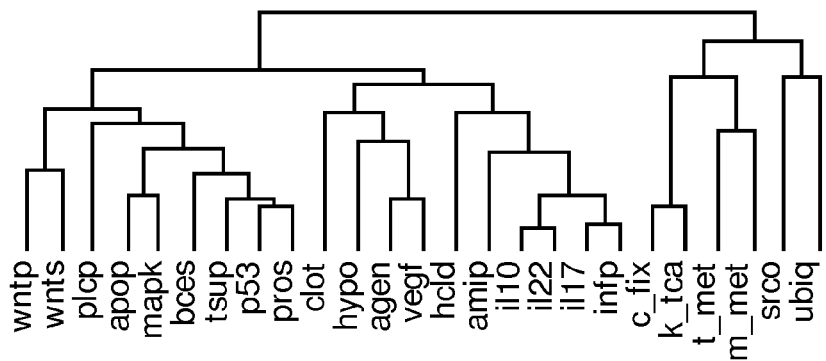
FIG. 2 is a dendrogram of ordered genetic information according to an embodiment.

In a step 130, the primary biological data is used to order the genetic information represented by the 25 gene sets according to table 1. The ordering may result in clusters of primary biological data. The resulting ordered genetic information from the ordering step 130 is shown in a dendrogram according to FIG. 2.

Figure 3:
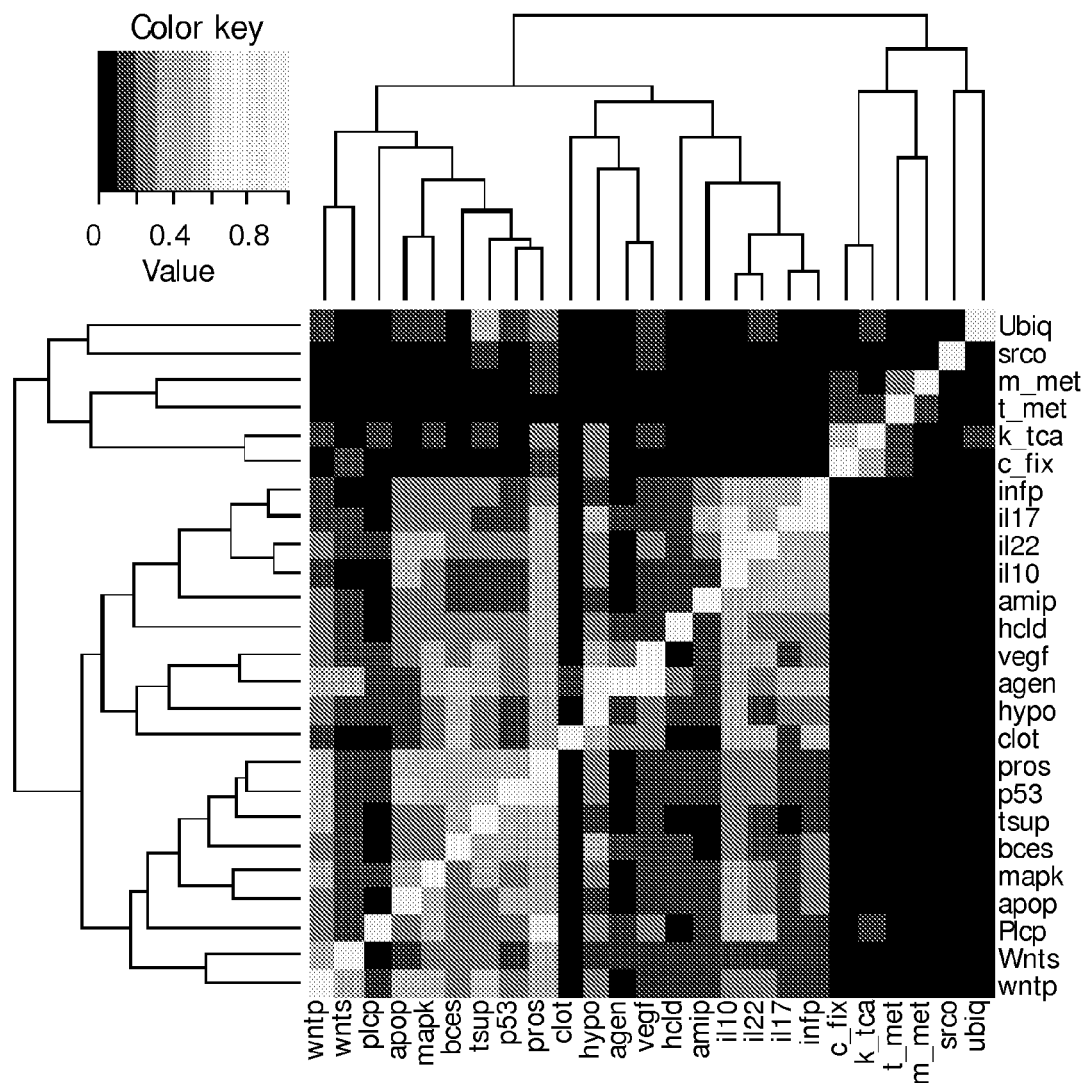
FIG. 3 is a matrix showing overlaps of the clustered information according to an embodiment.
Figure 4:
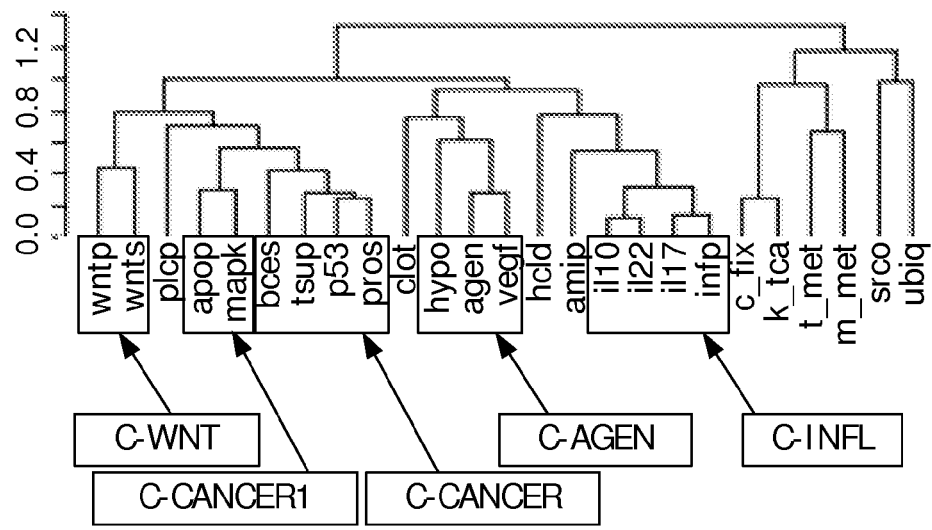
FIG. 4 is are thematic clusters according to an embodiment.

FIG. 3 is a matrix showing overlaps of the clustered information, when two clusters are plotted against each other. In FIG. 3, contiguous bright regions emerge along the diagonal that correspond to the strongest clusters in the dendrograms. From such highly-related gene sets, thematic clusters are created. Cancer-related, vasculature, and inflammation sets cluster together, which is evident from the structure of the dendrograms as well as the lit-up areas in FIG. 3. Furthermore, the control gene sets have practically no overlap with the cancer-related sets. The thematic clusters are shown more clearly in FIG. 4.

Next, multiple molecular signatures are obtained from a signature data repository in a step 140. In an embodiment, the signatures are obtained by choosing breast cancer prognosis gene expression signatures, well known to a person skilled in the art such as Veer, Wang, Caldas and Oncotype. Caldas refers to a prognostic signature of 70 genes that are significantly correlated with survival in early stage node-positive and node-negative tumors. The Veer signature is also a 70-gene-expression signature, which predicts the outcome of pre-menopausal, node-negative and node-positive breast cancer patients with more accuracy than conventional prognostic indicators. The Wang signature is a different 76-gene prognostic signature, which predicts outcome for pre-menopausal, node-negative breast cancer patients. Oncotype refers to a 21-gene-expression signature which predicts recurrence in tamoxifen-treated node-negative breast cancer.

Secondary biological data corresponding to each molecular signature is obtained from the knowledge database in a step 150.

The signatures are sorted in a step 160 according to the correspondence of said secondary biological data and said primary biological data, to form a ranking of said molecular signatures.

As an example, Table 2 shows the number of gene ontology (GO) biological process (BP) term identifiers that describe a subset of the gene sets, i.e. the four prognostic signatures.

TABLE 2

Identifier sets describe gene sets

|  | Number of GO BP term identifiers |
|---|---|
| CALDAS | 90 |
| ONCO | 176 |
| VEER | 61 |
| WANG | 119 |

Table 3 shows absolute similarity as intersection of identifier sets of gene sets. For example, the intersection of identifiers (GO terms) of gene set CALDAS and gene set apop (apoptosis) is 9.

TABLE 3

Absolute similarity between identifier sets of sample gene sets.

|  | apop | mapk | srco | wntp | wnts | ubiq | plcp | bces | tsup | p53 |
|---|---|---|---|---|---|---|---|---|---|---|
| CALDAS | 9 | 5 | 0 | 11 | 6 | 4 | 0 | 10 | 16 | 16 |
| ONCO | 57 | 37 | 0 | 35 | 13 | 5 | 16 | 60 | 37 | 74 |
| VEER | 2 | 3 | 0 | 3 | 6 | 2 | 1 | 5 | 12 | 6 |
| WANG | 10 | 20 | 1 | 11 | 5 | 7 | 1 | 31 | 14 | 17 |

Table 4 shows relative similarity and collective similarity. Relative similarity between gene set CALDAS and gene set apop is 0.1, which is the absolute similarity between CALDAS and apop (9), normalized by the number of identifiers in the gene set CALDAS (90). The collective similarity of gene set Caldas to the 10 column header gene sets is the row of values corresponding to CALDAS.

TABLE 4

Relative similarity and collective similarity between identifier sets of gene sets.

|  | apop | mapk | srco | wntp | wnts | ubiq | plcp | bces | tsup | p53 |
|---|---|---|---|---|---|---|---|---|---|---|
| CALDAS | 0.100008 | 0.055564 | 7.85E−06 | 0.12223 | 0.066685 | 0.044451 | 5.52E−06 | 0.111123 | 0.177784 | 0.177793 |
| ONCO | 0.323868 | 0.210241 | 5.00E−07 | 0.198869 | 0.073871 | 0.02841 | 0.090913 | 0.34091 | 0.210236 | 0.42046 |
| VEER | 0.032797 | 0.049183 | 2.95E−06 | 0.049188 | 0.098371 | 0.032793 | 0.01641 | 0.081986 | 0.196737 | 0.098372 |
| WANG | 0.084035 | 0.168072 | 0.008413 | 0.092444 | 0.042028 | 0.058826 | 0.008407 | 0.260518 | 0.117651 | 0.142861 |

Figure 5:
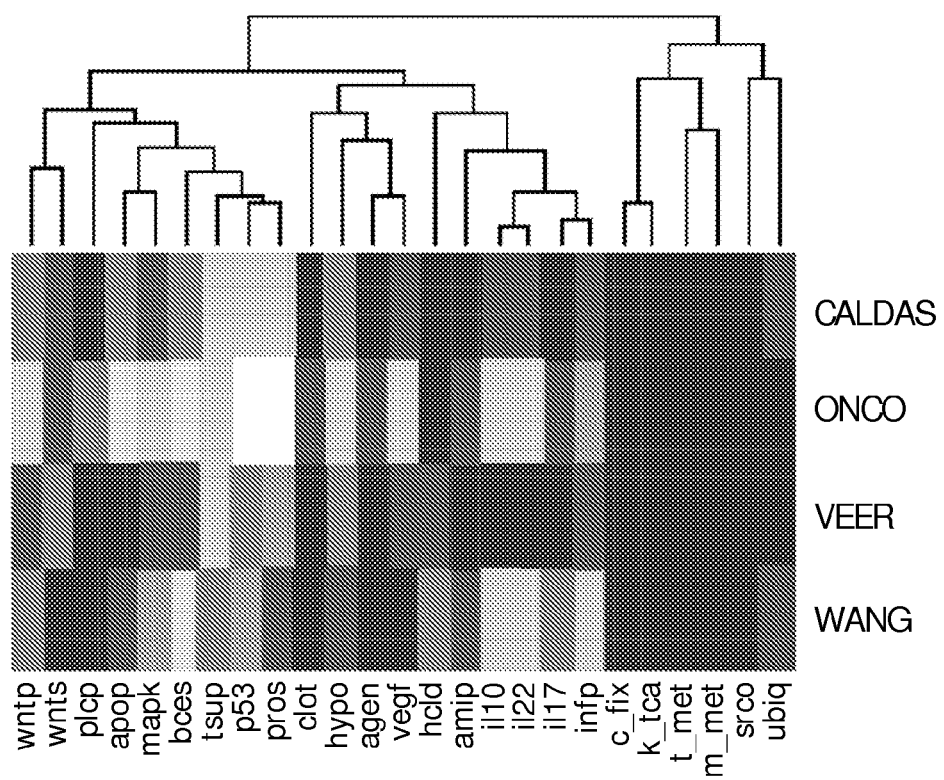
FIG. 5 is an overview of a thematic cluster and a dendrogram according to an embodiment.
Figure 6:
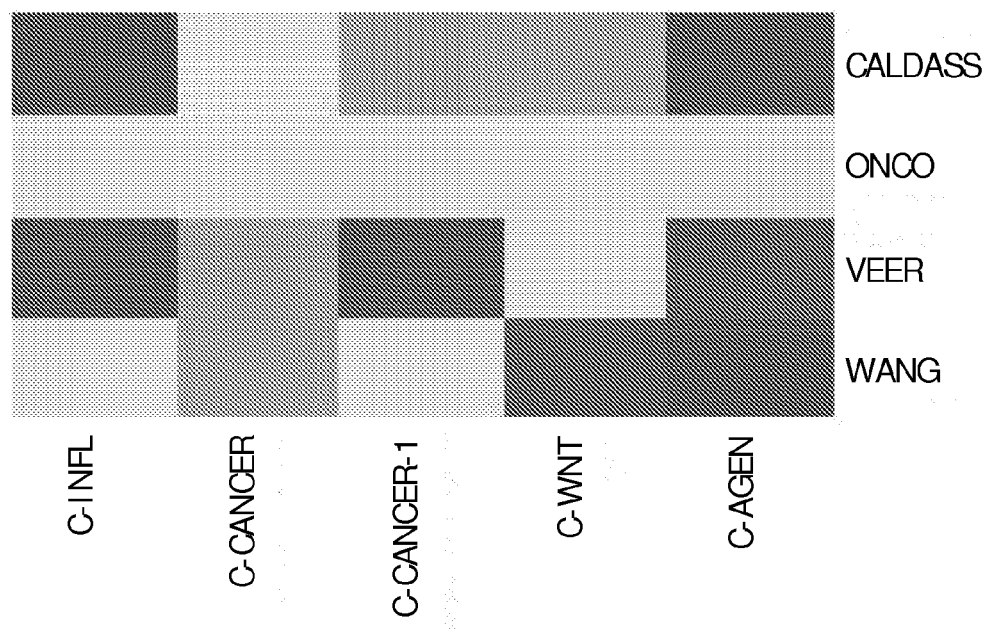
FIG. 6 is another an overview of a thematic cluster and a dendrogram according to an embodiment.

FIG. 5 illustrates the relationships shown in table 3 and 4 as sorted molecular signatures in relation to the gene sets. A pattern of overlaps between the four signatures (Veer, Wang, Caldas and Oncotype) and the cancer-related gene sets is shown. Additionally, there are no overlaps between the signatures and the control gene sets.

From FIG. 5, it may be seen how the molecular signatures may be ranked. For example, the C-CANCER thematic cluster, which consists of the gene sets: breast cancer estrogen signaling (bces), tumor suppressor (tsup), P53 pathway (p53), and pros-tate cancer-related (pros), has overlapping functional relationships compared to all signatures. The overlap of the Oncotype signature is substantially stronger relative to the remaining signature sets, suggesting that the Oncotype signature is a lot more specific to the cancer-related biological processes represented by the C-CANCER gene set. In addition, it may be seen that the overlaps amongst the Oncotype signature and the gene sets are mainly associated with processes such as apoptosis and programmed cell death, whereas the Caldas signature overlaps processes involved in cell cycle and cellular response to starvation and nutrient levels. Similarly, the Veer signature overlaps underline cell growth. In this way, the clusters of molecular signatures may be ranked based on what kind of information is needed.

Next, an output signal is generated in a step 170 based on said ordered genetic information and said ranking of the molecular signatures. The output signal may be sent to a decision support workstation. In an embodiment, said output signal may be a heat map. In another embodiment, the output signal may be a dendrogram.

The molecular signatures may be chosen from any source of molecular signatures known within the art, such as nucleotide sequence information, genetic variation information, methylation status information, or expression information. The molecular signature data may be any kind of molecular signature data known within the art, singly or in combination.

The primary biological data may be any kind of biological data known within the art, such as biological annotations, genomic annotations, gene ontology, molecular signatures, or specialized gene sets. The biological data may be any kind of biological data known within the art, singly or in combination.

Any combination of molecular signature information, singly or in combination, and primary biological data, singly or in combination, may be used.

Figure 7:
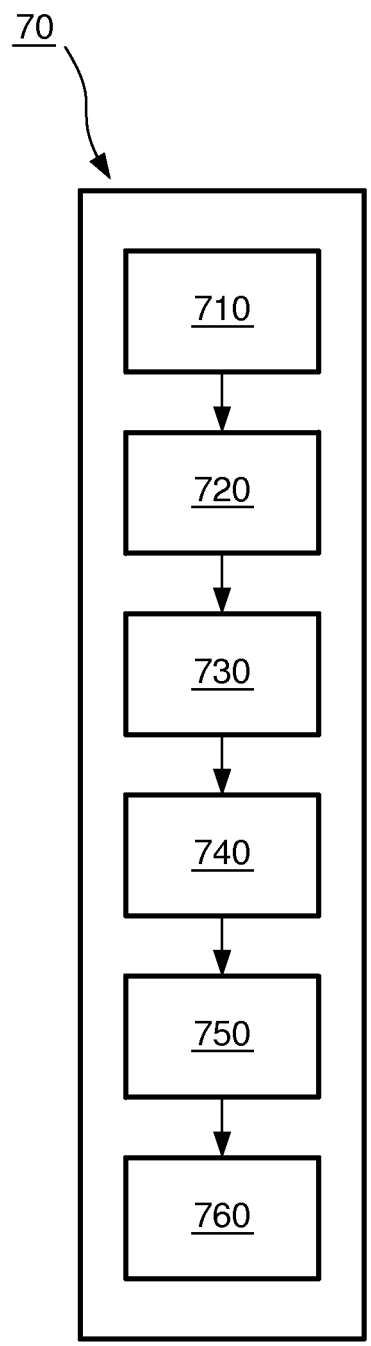
FIG. 7 is a flowchart of a device according to an embodiment.

In another embodiment of the invention according to FIG. 7, a device 70 for clinical decision support based on comparison of multiple molecular signatures is provided. Said device 70 comprises a first unit 710 configured to obtain genetic information. Furthermore, the device 70 comprises a second unit 720 configured to obtain primary biological data corresponding to the genetic information from a knowledge database. The device 70 also comprises a third unit 730 configured to order said genetic information according to the primary biological data. Also, the device 70 comprises a fourth unit 740 configured to obtain multiple molecular signatures from a signature data repository. The device 70 comprises a fifth unit 750 configured to obtain secondary biological data corresponding to each molecular signature from the knowledge database. Furthermore, the device 70 comprises a sixth unit 760 configured to sort according to the correspondence of said secondary biological data and said primary biological data, to form a ranking of said molecular signatures. The device 70 also comprises a seventh unit 770 configured to generate an output signal indicative of a clinical decision based on said ordered genetic information and said ranking of the molecular signatures.

The decision support workstation may be a single workstation, or multiple workstations positioned together or separately. In an embodiment, user access may be differentiated between multiple workstations, so that a workstation works only for reporting data and another workstation works only to request information or receive the output signal.

The units 710, 720, 730, 740, 750, 760, 770 are operatively connected to each other. The units 710, 720, 730, 740, 750, 760, 770 may be embodied as separate physical entities, connected together. However, the units 710, 720, 730, 740, 750, 760, 770 may also be embodied in a singular physical entity. Any combination of the units 710, 720, 730, 740, 750, 760, 770 may be embodied in different separate or unified physical entities. Said entities may further be combined in any setup, forming a connection between the physical entities.

Figure 8:
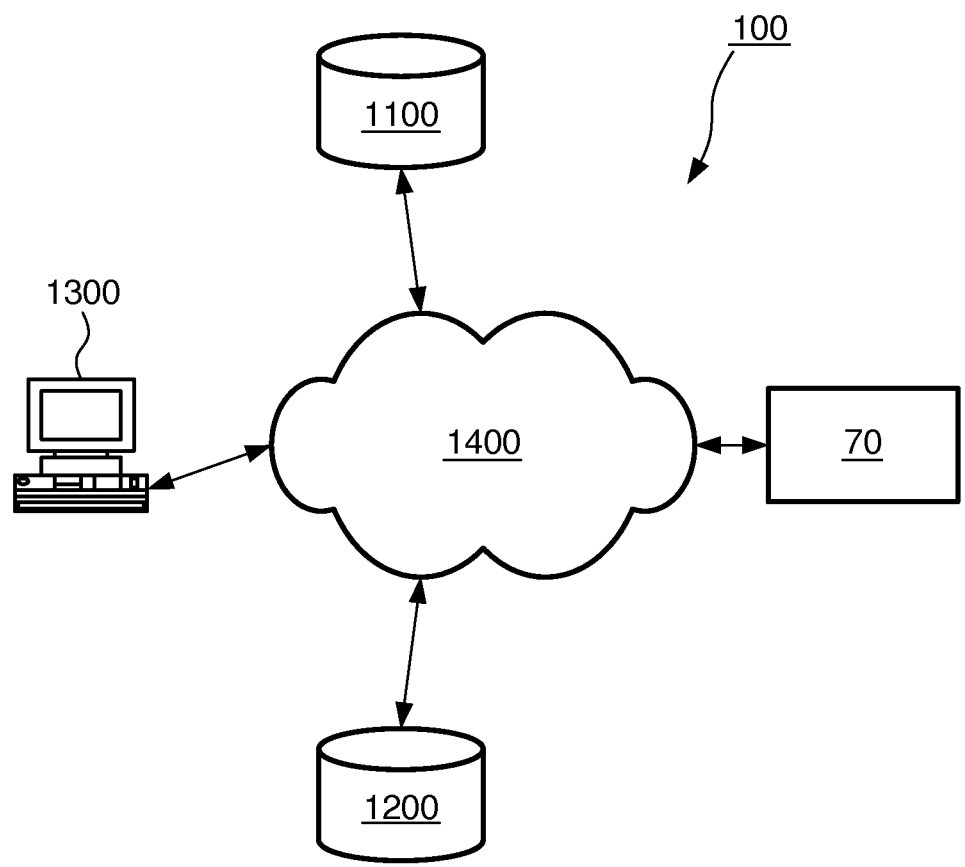
FIG. 8 is a system according to an embodiment.

In an embodiment according to FIG. 8, system 100 for clinical decision support is provided. Said system 100 comprises a device 70 according to embodiments provided herewith. Said system 100 also comprises a knowledge database 1100, where primary biological data is stored and accessed. Also, said system 100 comprises a signature data repository 1200, where secondary biological data is stored and accessed. Furthermore, the system 100 also comprises a workstation 1300, from which a user may enter information, operate the system 100 or interpret the output signal provided by the system 100. Said device 70, knowledge database 1100, signature data repository 1200 and workstation 1300 are operatively connected by a connecting network 1400.

The workstation 1300 may be a single workstation, or multiple workstations positioned together or separately. In an embodiment, user access may be differentiated between multiple workstations, so that a workstation works only for reporting data and another workstation works only to request information or receive the output signal.

The repository 1200 may comprise data from multiple subjects, such as molecular signature data, scientific reports, test data, such as data from clinical studies, patient data, etc.

The knowledge database 1100 may comprise data regarding biological annotations, such as methylation, transcription regulatory information or genetic variation, biological ontology data, such as GO data, molecular signature ontology data etc.

In an embodiment, the method 10, device 70 or system 100 provides information, such as ordered genetic information or ranking that may assist a physician in reaching a diagnosis or treating a patient.

In an embodiment, the device 70 or system 100 is connected to a hospital information system (HIS), a laboratory information system (LIS), a clinical department information system, a drug knowledge database, a pharmacy information system etc.

The method 10, device 70 or system 100 may enable selection of biologically and clinically relevant molecular signatures or comparing new signatures to existing established and validated tests. An additional level of interpretation of molecular diagnostic tests is provided compared to the prior art, based on the multi-valued signatures, such as biomarkers, according to embodiments provided herewith. Further interpretation of diagnostic test results is obtained. This is an advantage compared to the prior art, which only obtains simple indication of the status of the test being performed. This makes it possible to convert results from simple tests into actions, such as what other tests need to be performed. Furthermore, in an embodiment, prior art tests may be applied beyond their original scope. For example, if a subject is indicated for a disease based on one or more tests, based on signatures discovered in studies of different demographics, it may be possible to utilize such less confident signatures with other established signatures for the correct patient demographics. That is, if the subject is of a demographic background entirely different than the demographics of the subjects used in the clinical studies of the prior art test, it may be possible to indirectly assess how close the indicative tests/signatures are to ones relevant for the subject.

For example, if a subject is diagnosed with breast cancer, a physician may want to have an indication regarding the aggressiveness of the disease. For this purpose, the physician orders molecular signature-based tests A, B, C and D to be performed on biopsies from the subject. The results are negative for C, B and D but positive for A. The physician then performs an analysis according to the method 10 and finds that tests C, B and D are grouped together and have the same underlying biology. Further research regarding the study behind test A, using the device 70 or the system 100, shows that the subject population is based solely on a northern European population. The subject is Chinese, whereby the physician concludes that difference in ethnicity might be the reason behind the conflicting result. The physician thus decides to order tests E and F to confirm the pathobiology of the disease and eventually selects therapy X and Y-specific to the presentation of the disease in the subject.

This shows that embodiments of the method 10, device 70 or system 100 may enable clinically useful conclusions both based on agreements and disagreements between tests. The analysis may be repeated for a different context and may then provide another valuable angle to the disease, condition or symptoms of the subject.

Applications and use of the above described the method 10, device 70 or system 100 according to embodiments provided herewith are various and include fields like data mining, research, aid in finding eligible subject for clinical trials clinical support, information about correlations between methods of treatment, information about how drugs effect phenotypes etc.

The units 710, 720, 730, 740, 750, 760, 770 may be any units normally used for performing the involved tasks, e.g. a hardware, such as a processor with a memory.

In an embodiment the device 70 or the system 100 is comprised in a medical workstation or medical system, such as a Computed Tomography (CT) system, Magnetic Resonance Imaging (MRI) System or Ultrasound Imaging (US) system.

Figure 9:
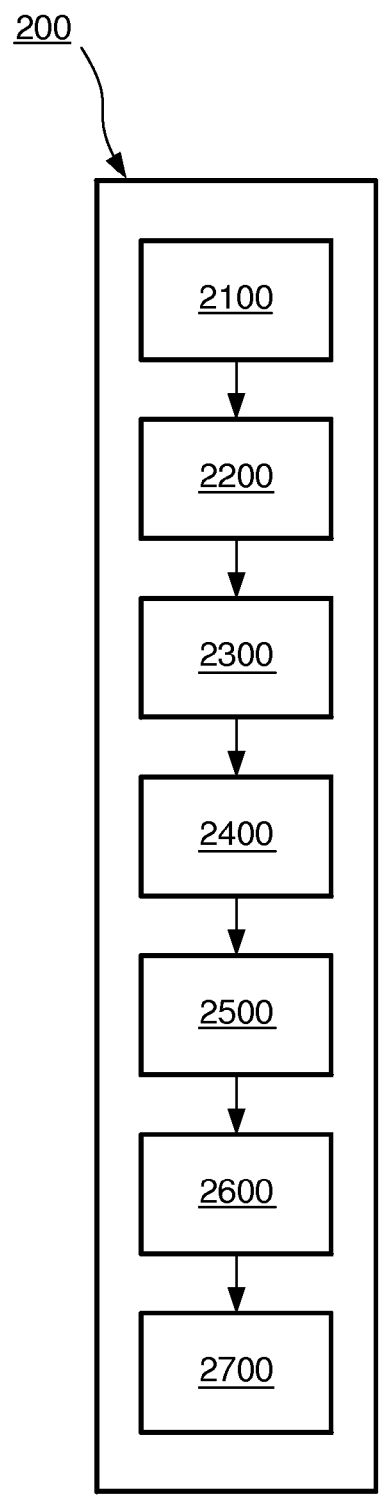
FIG. 9 is a flowchart of a computer-readable medium according to an embodiment.

In an embodiment according to FIG. 9, a computer-readable medium has embodied thereon a computer program 200 for processing by a computer. The computer program 200 comprises a first code segment 2100 for obtaining genetic information. The computer program 200 further comprises a second code segment 2200 for obtaining primary biological data corresponding to the genetic information from a knowledge database. The computer program 200 also comprises a third code segment 2300 for ordering said genetic information according to the primary biological data. Furthermore, the computer program 200 comprises a fourth code segment 2400 for obtaining multiple molecular signatures from a signature data repository. The computer program 200 also comprises a fifth code 2500 segment for obtaining secondary biological data corresponding to each molecular signature from the knowledge database. Also, the computer program 200 comprises a sixth code segment 2600 for sorting said molecular signatures according to the correspondence of said secondary biological data and said primary biological data, to form a ranking of said molecular signatures. The computer program 200 also comprises a seventh code segment 2700 for generating an output signal indicative of a clinical decision based on said ordered genetic information and said ranking of the molecular signatures.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for clinical decision support based on comparison of multiple molecular signatures, the method comprising the steps of:
    obtaining, by a processing device, genetic information;
    obtaining, by the processing device, primary biological data corresponding to the genetic information from a gene ontology knowledge database;
    ordering, by the processing device, the genetic information according to the primary biological data to form gene clusters;
    obtaining, by the processing device, multiple molecular signatures from a signature data repository, each molecular signature corresponding to a prognosis gene expression signature for a particular illness;
    obtaining, by the processing device, secondary biological data corresponding to each molecular signature from the gene ontology knowledge database;
    determining correspondence between the secondary biological data and the primary biological data;
    sorting, by the processing device, the molecular signatures according to the correspondence of the secondary biological data and the primary biological data, to form a ranking of the molecular signatures that indicates a correspondence between each molecular signature and the gene clusters; and
    generating, by the processing device, an output signal indicative of a clinical decision based on the ordered genetic information and the ranking of the molecular signatures.

2. The method according to claim 1, wherein the genetic information is derived from a single subject.

3. The method according to claim 1, wherein the molecular signatures are chosen from the group comprising: nucleotide sequence, genetic variation, methylation status, or expression.

4. The method according to claim 1, wherein the primary biological data is chosen from the group comprising: biological annotations, genomic annotations, gene ontology, molecular signatures, or specialized gene sets.

5. The method according to claim 1, wherein the secondary biological data is chosen from the group comprising: gene ontology, molecular signatures, or pathway information.

6. A device for clinical decision support based on comparison of multiple molecular signatures, the device comprising:
    a first unit configured to obtain genetic information;
    a second unit configured to obtain primary biological data corresponding to the genetic information from a gene ontology knowledge database;
    a third unit configured to order the genetic information according to the primary biological data to form gene clusters;
    a fourth unit configured to obtain multiple molecular signatures from a signature data repository, each molecular signature corresponding to a prognosis gene expression signature for a particular illness;
    a fifth unit configured to obtain secondary biological data corresponding to each molecular signature from the gene ontology knowledge database;
    a sixth unit configured to determine correspondence between the secondary biological data and the first biological data, and to sort the molecular signatures according to the correspondence of the secondary biological data and the primary biological data, to form a ranking of the molecular signatures that indicates a correspondence between each molecular signature and the gene clusters; and
    a seventh unit configured to generate an output signal indicative of a clinical decision based on the ordered genetic information and the ranking of the molecular signatures, wherein the units being operatively connected to each other.

7. A system for clinical decision support based on comparison of multiple molecular signatures, the system comprising:
    a device comprising:
        a first unit configured to obtain genetic information;
        a second unit configured to obtain primary biological data corresponding to the genetic information from a gene ontology knowledge database;
        a third unit configured to order the genetic information according to the primary biological data to form gene clusters;
        a fourth unit configured to obtain multiple molecular signatures from a signature data repository, each molecular signature corresponding to a prognosis gene expression signature for a particular illness;
        a fifth unit configured to obtain secondary biological data corresponding to each molecular signature from the gene ontology knowledge database;
        a sixth unit configured to determine correspondence between the secondary biological data and the first biological data, and to sort the molecular signatures according to the correspondence of the secondary biological data and the primary biological data, to form a ranking of the molecular signatures that indicates a correspondence between each molecular signature and the gene clusters; and a seventh unit configured to generate an output signal indicative of a clinical decision based on the ordered genetic information and the ranking of the molecular signatures, wherein the units are operatively connected to each other;

the gene ontology knowledge database;

the signature data repository; and a decision support workstation, wherein the device, knowledge database, signature data repository and decision support workstation are operatively connected by a connecting network.

8. A non-transitory computer-readable medium having embodied thereon a computer program for processing by a computer, the computer program comprising:

a first code segment for obtaining genetic information;

a second code segment for obtaining primary biological data corresponding to the genetic information from a gene ontology knowledge database;

a third code segment for ordering the genetic information according to the primary biological data to form gene clusters;

a fourth code segment for obtaining multiple molecular signatures from a signature data repository, each molecular signature corresponding to a prognosis gene expression signature for a particular illness;

a fifth code segment for obtaining secondary biological data corresponding to each molecular signature from the gene ontology knowledge database;

a sixth code segment for determining correspondence between the secondary biological data and the first biological data, and for sorting the molecular signatures according to the correspondence of the secondary biological data and the primary biological data, to form a ranking of the molecular signatures that indicates a correspondence between each molecular signature and the gene clusters; and a seventh code segment for generating an output signal indicative of a clinical decision based on the ordered genetic information and the ranking of the molecular signatures.

9. A non-transitory computer-readable medium that includes a program that, when executed by a processor, causes the processor to:

obtain genetic information;

obtain primary biological data corresponding to the genetic information from a gene ontology knowledge database;

order the genetic information according to the primary biological data to form gene clusters;

obtain multiple molecular signatures from a signature data repository, each molecular signature corresponding to a prognosis gene expression signature for a particular illness;

obtain secondary biological data corresponding to each molecular signature from the gene ontology knowledge database;

determine correspondence between the secondary biological data and the first biological data;

sort the molecular signatures according to the correspondence of the secondary biological data and the primary biological data, to form a ranking of the molecular signatures that indicates a correspondence between each molecular signature and the gene clusters; and generate an output signal indicative of a clinical decision based on the ordered genetic information and the ranking of the molecular signatures.

\* \* \* \* \*